United States Patent [19]
Koyama et al.

[11] Patent Number: 5,654,152
[45] Date of Patent: Aug. 5, 1997

[54] METHOD OF MEASURING ENZYME ACTIVITY BY USING A COLUMN HAVING AN IMMOBILIZED SUBSTRATE

[75] Inventors: Tamami Koyama; Soyao Moriguchi; Hiroshi Suzuki, all of Tokyo, Japan

[73] Assignee: Showa Denko Kabushiki Kaisha, Tokyo, Japan

[21] Appl. No.: 479,841

[22] Filed: Jun. 7, 1995

Related U.S. Application Data

[63] Continuation of Ser. No. 164,841, Dec. 9, 1993, abandoned, which is a continuation of Ser. No. 905,218, Jun. 29, 1992, abandoned, which is a continuation of Ser. No. 771,836, Oct. 8, 1991, abandoned, which is a continuation of Ser. No. 312,997, Feb. 21, 1989, abandoned.

[30] Foreign Application Priority Data

| Feb. 19, 1988 | [JP] | Japan | 63-36987 |
| Oct. 4, 1988 | [JP] | Japan | 63-250340 |
| Dec. 16, 1988 | [JP] | Japan | 63-316156 |
| Jan. 13, 1989 | [JP] | Japan | 1-7065 |

[51] Int. Cl.$^6$ .................................... C12Q 1/68
[52] U.S. Cl. .................... 435/6; 435/5; 435/7.1; 435/8; 435/9; 435/10; 435/11; 435/12; 435/13; 435/14; 435/15; 435/16; 435/17; 435/18; 435/19; 435/20; 435/21; 435/22; 435/23; 435/24; 435/25; 435/26; 435/27; 435/28; 435/810; 436/501; 536/24.1; 536/24.3; 536/24.31; 536/24.32; 536/24.33; 935/77; 935/78
[58] Field of Search ................ 435/5, 6, 7.1, 810, 435/8–28; 436/501; 536/24.1, 24.3–.33; 935/77, 78

[56] References Cited

U.S. PATENT DOCUMENTS

| 3,933,589 | 1/1976 | Keyes | 195/68 |
| 4,046,633 | 9/1977 | Keutel | 195/103.5 R |
| 4,169,765 | 10/1979 | Keyes | 435/291 |
| 4,172,765 | 10/1979 | Keyes | 435/14 |
| 4,299,916 | 11/1981 | Litman et al. | 435/6 |
| 4,337,309 | 6/1982 | McGeeney | 435/22 |
| 4,415,631 | 11/1983 | Schutigser | 428/405 |
| 4,517,241 | 5/1985 | Alpert | 428/332 |
| 4,859,581 | 8/1989 | Nicolson et al. | 435/4 |
| 4,894,468 | 1/1990 | Wilchels et al. | 556/416 |
| 4,973,577 | 11/1990 | Vale, Jr. et al. | 514/12 |

FOREIGN PATENT DOCUMENTS

A2019256  10/1979  United Kingdom.

OTHER PUBLICATIONS

TRAC: Trends in Analytical Chemistry, vol. 5, No. 7, Aug., 1986, pp. 185–189, Amsterdam, NL; L. Dalgaard, "Immobilized Enzymes as Post–Column Reactors in High–Performance Liquid Chromatography".

*Primary Examiner*—Ardin H. Marschel
*Attorney, Agent, or Firm*—Sughrue, Mion, Zinn, Macpeak & Seas

[57] ABSTRACT

Enzyme activity is measured promptly with a high accuracy by introducing an enzyme, the activity of which is to be measured, into a column comprising a hollow tube packed with a filler comprising a support and a substrate that can be recognized by the enzyme, which is immobilized on the support, and measuring the amount of the obtained decomposition product of the substrate.

5 Claims, 13 Drawing Sheets

METHOD OF MEASURING ENZYME ACTIVITY BY USING A COLUMN HAVING AN IMMOBILIZED SUBSTRATE

This is a continuation of application Ser. No. 08/164,841 filed Dec. 9, 1993, now abandoned, which is in turn a continuation of application Ser. No. 07/905,218 filed on Jun. 29, 1992, now abandoned, which is in turn a continuation of application Ser. No. 07/771,836 filed on Oct. 8, 1991, now abandoned, which is in turn a continuation of application Ser. No. 07/312,997 filed on Feb. 21, 1989, now abandoned.

BACKGROUND OF THE INVENTION (1) Field of the Invention

The present invention relates to a filler for measuring the enzyme activity, an enzyme activity-measuring column packed with the filler, and a method of measuring the enzyme activity by using the column.

(2) Description of the Related Art

It is known that an enzyme is a protein synthesized by living cells, and the catalytic action of the enzyme to a living body reaction is important for the maintenance of life. In the natural state, millions of enzymes originating in animals, plants and micro-organisms exist, and about 2,000 of these enzymes have been isolated and are used as industrial enzymes in the fields of foodstuffs and detergents or as medicinal enzymes for remedy of diseases and clinical examination, and recently, in the field of genetic engineering.

The measurement of the activity of an enzyme is made by measuring the catalytic activity of the enzyme and obtain a basic index showing the function of the enzyme. In the conventional method, the enzyme activity is measured by analyzing the decrease in the amount of a substrate or the increase in the amount of a product. More specifically often adopted are a method in which the decrease in the amount of a substrate or the increase in the amount of a product after the reaction by an enzyme is measured as the absorbance by a spectrophotometer, a method in which the measurement is carried out by coloration of a substrate or product by a chemical reagent, and a method in which a product is converted to a coloring substance and the measurement is effected on the formed coloring substance. Moreover, a method is known in which a substrate is labelled with a radioactive element and the labelled substrate is detected. In general, however, these methods have problems in that a large quantity of the enzyme is necessary for the measurement, the chemical reagent used is expensive, many kinds of chemical reagents are necessary, a long time is required for the measurement, a high degree of skill is needed when making the measurement, and the measurement is easily influenced by impurities. Accordingly, it is difficult to obtain an accurate value.

As the means for coping with these defects, a method has been proposed in which the measurement is combined with liquid chromatography, i.e., an enzyme is separated and purified by a column and after elution from the column, the enzyme is placed in contact with a substrate solution, and the decrease in the amount of the substrate determined [H. A. Chase: J. Chem. Tech. Biotechnol., 36, 351 (1986), and N. Ito et al: J. Chromatogr., 400, 163 (1987)] this method is still unsatisfactory in that high-purity and expensive reagents must be continuously supplied and an additional device such as a pump must be used to ensure this continuous supply.

SUMMARY OF THE INVENTION

Therefore, a primary object of the present invention is to overcome the defects of the conventional methods of measuring the enzyme activity and to provide a filler for the measurement of the enzyme activity, by which it is possible to measure the enzyme activity simply and promptly with a high accuracy, a column packed with this filler, and a method of measuring the enzyme activity by using this packed column.

According to the present invention, there are provided a filler for measuring the enzyme activity, a column packed with this filler, and a method of measuring the enzyme activity by using this packed column, by which the foregoing object is attained.

More specifically, in accordance with one aspect of the present invention, there is provided a filler for measuring the enzyme activity, which comprises a support and a substrate that can be recognized by an enzyme, which is immobilized on the support.

In accordance with another aspect of the present invention, there is provided a column for measuring the enzyme activity, which comprises a hollow tube packed with a filler comprising a support and a substrate that can be recognized by an enzyme, which is immobilized on a support.

In accordance with still another aspect of the present invention, there is provided a method for measuring the enzyme activity, which comprises introducing an enzyme, the activity of which is to be measured, into a column comprising a hollow tube packed with a filler comprising a support and a substrate that can be recognized by the enzyme, which is immobilized on the support, and measuring the amount of the obtained decomposition product of the substrate.

DESCRIPTION OF THE PREFERRED EMBODIMENTS

Figure 1:
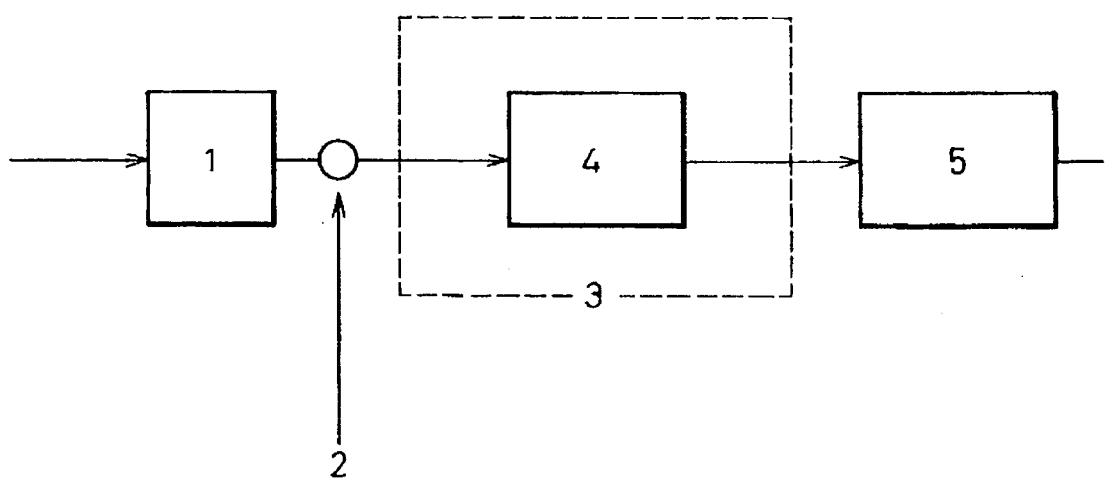
FIG. 1 illustrates an example of the apparatus for measuring the enzyme activity according to the present invention, wherein 1 represents a pump, 2 represents a sample, 3 represents a thermostat oven, 4 represents a column of a support having a substrate immobilized thereon, and 5 represents a detector.

The enzyme activity-measuring filler of the present invention, a column packed with this filler and a method for measuring the enzyme activity by using this packed column will now be described.

The enzyme activity-measuring filler of the present invention is prepared by immobilizing a substrate that can be recognized by an enzyme on a water-insoluble support.

Either a porous support or a non-porous support can be used in the present invention. For example, there can be mentioned soft beads of polysaccharides such as cellulose, agarose and dextran and polyacrylamide, silica gels, and beads of synthetic polymers such as styrene polymers, vinyl alcohol polymers, acrylate polymers and methacrylate polymers, which have often been used for support of separation columns. But, for high-speed liquid chromatography (HPLC), hard beads such as silica gels and synthetic polymer beads are preferable. The particle size is not particularly critical, but preferably the particle size is from 3 to 100 μm.

For bonding a substrate that can be recognized by an enzyme to the support, first a binding group having a functional group to which the substrate can be covalently bonded must be bonded to a binding group-introducing group possessed by the support, such as a hydroxyl group.

As the functional group to which the substrate is bonded, there can be mentioned, for example, an epoxy group, an amino group, a hydrazino group, a carboxyl group, and a formyl group. The introduction of the binding group having a functional group as mentioned above into the support can be easily accomplished in the presence of an appropriate solvent by a known method. As the epoxy group-containing binding group, there can be mentioned, for example, epihalohydrins such as epichlorohydrin, diglycidyl ethers such as 1,4-butanediol diglycidyl ether, and diepoxides such as 1,7-octadiene diepoxide. A binding group of this type promptly reacts with the hydroxyl group on the support under an alkaline condition to give an epoxy-modified support. An amino-modified support having an amino group is obtained by reacting the obtained epoxymodified support with ammonia, hydrazine or a diaminoalkane such as 1,3-propanediamine, and a carboxyl-modified support is obtained by reacting the epoxy-modified support with an aminocarboxylic acid such as 4-aminobutyric acid. Furthermore, a formyl-modified support is obtained by hydrolyzing the epoxy group and oxidizing the hydrolyzed group with periodic acid. Moreover, when the amino-modified support is reacted with an acid anhydride such as succinic anhydride, a carboxyl-modified support is obtained.

Bonding of a substrate that can be recognized by an enzyme to this functional group-containing support can be carried out in an appropriate solvent, if necessary by using an appropriate catalyst or reactant according to the kind of functional group possessed by the binding group. For example, when the functional group is an epoxy group, an acid or alkali such as hydrochloric acid, sodium carbonate or sodium hydrogencarbonate is mainly used as the catalyst. When the functional group is a carboxyl group, a condensing agent such as N-hydroxysuccinimide, dicyclohexylcarbodiimide or 1-ethyl-3-(3-dimethylaminopropyl)-carbodiimide is used as the reactant, and when the functional group is a formyl group, a reducing agent such as sodium cyano borohydride is used. Water is generally used as the solvent, and buffer solutions such as phosphate buffer or acetate buffer can be used according to need. Furthermore, an inorganic salt such as sodium chloride can be added to water as the solvent.

The length of the binding group is not particularly critical, but a length corresponding to 6 to 30 atoms is preferred.

The substrate that can be recognized by an enzyme and that is immobilized on the functional group-containing support is not particularly critical, so long as the substrate is capable of forming a substrate decomposition product by contact with the objective enzyme, the activity of which is to be measured. As typical instances of the substrate, there can be mentioned glucose, cholesterol, choline, uric acid, amines such as benzylamine and histamine, xanthine, acetylcholine, glutathione, thymidine-5'-phosphate, chondroitin sulfate, (deoxy)ribonucleic acid, a cholesterol ester, a phosphoric acid monoester such as bis-p-nitrophenyl phosphate, amino acids such as arginine, lysine and tyrosine, an oligopeptide having a specific amino acid at the C-terminal such as phenylalanylarginine, to which a labelled compound such as p-nitrophenyl group or glycylglutamic acid is bonded, a synthetic substrate such as benzoylarginine ethyl ester, compounds in which α-(β-)glucose, α-(β-)galactose, α-(β-)mannose, β-fructose, α,α-trehalose, β-glucuronic acid or α-L-fucose is glucoside-bonded to other saccharide such as glucose or a labelled compound such as methylumbelliferone, and cellulose, chitin, dextran, starch, heparin, and fructose-1,6-bisphosphate.

The amount of the substrate supported on the support is 0.01 µmole/g to 5 mmole/g, preferably 0.1 µmole/g to 1 mmole/g, based on the dry gel.

The enzyme activity-measuring filler comprising the substrate that can be recognized by the enzyme, which is immobilized on the support, is packed in a hollow tube by customary procedures, and is used in the form of an enzyme activity-measuring column.

The hollow tube in which the enzyme activity-measuring filler is to be packed is generally a glass tube, a stainless steel tube, a titanium tube, a synthetic polymer tube such as a polycarbonate tube or a Teflon tube, or a stainless steel tube having an inner wall covered with Teflon. The size of the hollow tube is not particularly critical but is appropriately decided according to the intended object.

The enzyme activity-measuring filler can be packed into the hollow tube by customary procedures, and the packing method is not particularly critical. The pack ratio is appropriately selected.

The measurement of the enzyme activity by using the enzyme activity-measuring column according to the present invention is accomplished by introduction an enzyme to be measured into the column and measuring the amount of substrate decomposition product obtained. Namely, when an objective enzyme to be measured is injected into the enzyme activity-measuring column, while the enzyme is passing through the column, a substrate decomposition product is formed in an amount corresponding to the activity of the objective enzyme, and the formed substrate decomposition product can be detected by a detector for detecting the ultraviolet or visible absorption, fluorescent absorption or refractive index, or an electrochemical detector.

The apparatus to be used for the above-mentioned measurement comprises a liquid supply pump, a sampling valve, a column having a hollow tube packed with a filler comprising a support and a substrate that can be recognized by an enzyme, which is immobilized on the support, and a detector for detecting a substrate decomposition product. An example of this apparatus is illustrated in FIG. 1. The apparatus shown in FIG. 1 comprises a liquid supply pump 1, a sampling valve 2, a thermostat oven 3, a column 4 of a substrate-immobilized support, and a detector 5 for detecting a substrate decomposition product.

In the enzyme activity-measuring apparatus of the present invention, a separation column for the gel filtration chromatography, ion exchange chromatography, hydrophobic chromatography, partition adsorption chromatography or affinity chromatography can be disposed upstream and or downstream of the column of the substrate-immobilized support. An example of the measurement apparatus of this type is diagrammatically illustrated in FIG. 6. The apparatus comprises a liquid supply pump 1, a sampling valve 2, a thermostat tank 3, a column 4 of a substrate-immobilized support, a separation column 6 and a detector 5.

Furthermore, the enzyme activity-measuring apparatus of the present invention may be provided, in addition to a detector for detecting a decomposition product of the substrate, with a detector for detecting the enzyme per se, and further with a detector for detecting the other substrates in a sample, and monitors for monitoring ion strength and pH of an eluant.

The measurement temperature is not particularly critical, but preferably is 4° to 60° C. The kind of objective enzyme, the activity of which is to be measured, is not particularly critical, and the present invention can be applied to all enzymes. The objective enzyme can be purified single enzyme or a crude enzyme. Furthermore, the present invention can be applied to the measurement of one component present in a living body sample. Where other substances such as foreign proteins are present in a sample, the above-mentioned separation column for the gel filtration chromatography, ion exchange chromatography, hydrophobic chromatography or the like can be used in combination with the column of the substrate-immobilized support. In this method, simultaneously with the measurement of the enzyme activity, the portion of the peak separated by the separation column, where the activity is present, can be directly recognized. Moreover, if a high-speed liquid chromatography apparatus is assembled in the measurement apparatus, the enzyme activity can be easily measured at a high sensitivity with a small amount of a sample and within a short time. Furthermore, other various separation columns can be advantageously combined with the measurement apparatus.

The kinds of enzyme and substrate immobilized on the support are not particularly critical in the present invention, so long as a substrate decomposition product is formed by contact therebetween. For example, when the objective enzyme, the activity of which is to be measured, is an oxidoreductase, a transferase, a hydrolase or a lyase, preferably the substrates described below are combined with the objective enzyme, and a substrate decomposition product formed by this enzyme-substrate system is detected by a method as described below.

As the substrate for an oxidase such as glucose oxidase, cholesterol oxidase, choline oxidase, uric acid oxidase, an amine oxidase or xanthine oxidase, there can be mentioned glucose, cholesterol, choline, uric acid, an amine such as benzylamine or histamine, or xanthine, respectively. The substrate decomposition product formed in this system is mainly hydrogen peroxide, and this substrate decomposition product can be easily detected and measured, for example, by electrochemical means.

As the hydrolase, there can be mentioned an esterase, a protease and a glycosidase. The kind of esterase is not particularly critical. As the substrates corresponding to acetylcholine esterase, glutathione thiol ester hydrolase, phosphodiesterase I, chondroitin sulfatase, nuclease such as (deoxy)ribonuclease I or II, cholesterol esterase and alkali phosphatase, there can be mentioned acetylcholine, glutathione, thymidine-5'-phosphate, (deoxy)ribonucleic acid, cholesterol ester and a phosphoric acid ester such as bis-p-nitrophenyl phosphate, respectively. As the substrate decomposition product formed in this system, there can be mentioned choline, glutathione, thymidine, chondroitin, nucleotide, cholesterol and p-nitrophenol. These substances can be detected and measured by ultraviolet or visible absorption or fluorescent absorption or based on the change of the refractive index or the like.

As the substrate for a protease such as trypsin, plasmin, urokinase, bromelain, pronase, chymopapain, pepsin, chymotrypsin and thrombin, there can be mentioned amino acids having a specificity to an objective enzyme, such as arginine, lysine and tyrosine, and oligopeptides having a specific amino acid such as phenylalanylserylarginine at the C terminal to which a labelled compound such as a p-nitrophenyl group is bonded [hereinafter referred to as "substrate (A)"], ester-bonded oligopeptides such as glycidylglutamic acid [hereinafter referred to as "substrate (B)"], and synthetic substrates such as benzoylarginine ethyl ester [hereinafter referred to as "substrate (C)"]. In the case of proteases, the labelled compound or oligopeptide bonded to the specific amino acid is formed in the system (A) or (B), or the decomposition product of the synthetic substrate is formed in the system (C). An appropriate means can be selected according to the properties of the formed compound. For example, when the decomposition product is a labelled compound, a compound having an ultraviolet or visible absorption, such as p-nitrophenol or p-nitroaniline, is detected and measured by an ultraviolet or visible spectrophotometer. A compound having a fluorescence, such as 4-amino-methylcumarine, is detected and measured by a fluorescent photometer. When an oligopeptide or a decomposition product of a substrate having a benzoyl or dansyl group is formed, the formed compound is detected and measured by an ultraviolet spectrophotometer or a refractometer.

As the glycosidase, there can be mentioned $\alpha$-($\beta$-)glucosidase, $\alpha$-($\beta$-)galactosidase, $\alpha$-($\beta$)mannosidase, $\beta$-fructosidase, $\alpha,\alpha$-trehalase, $\beta$-glucronidase and $\alpha$-(L-)fucosidase, and as substrates for these glycosidases, there can be mentioned compounds in which $\alpha$-($\beta$-)glucose, $\alpha$-($\beta$-)galactose, $\alpha$-($\beta$-)mannose, $\beta$-fructose, $\alpha,\alpha$-trehalose, $\beta$-glucuronic acid and $\alpha$-L-fucose, respectively, are glucoside-bonded to other saccharide such as glucose or a labelled compound such as methylumbelliferone. As the substrate for a glucosidase having a specificity to a polysaccharide, such as cellulase, chitinase, dextranase, diastase or heparinase, there can be mentioned cellulose, chitin, dextran, starch, and heparin.

In the case of these glycosidases, when the decomposition product is a saccharide, the formed compound is detected and measured by a refractometer, and when the decomposition product is a labelled compound having an ultraviolet or visible absorption or fluorescent absorption, the formed compound is detected and measured by an ultraviolet or visible spectrophotometer or a fluorescent photometer.

As the lyase, there can be mentioned an aldolase such as fructose bisphosphate aldolase. In this case, fructose-1,6-bisphosphate or the like is used as the substrate, and dihydroxyacetone phosphate or glyceraldehyde-3-phosphate as the decomposition product is detected and measured by an ultraviolet spectrophotometer or a refractometer.

Where the objective enzyme, the activity of which is to be measured, still shows an activity in the presence of an activity inhibitor for the enzyme by an enzyme having a free active site, the residual activity can be measured by the substrate-immobilized support of the present invention.

The kind of the enzyme inhibitor to be made present is not particularly critical, and known substances derived from either natural products or synthetic compounds can be used, regardless of the inhibition mode. As the metal- or inorganic element-containing compound, there can be mentioned iodoacetic acid and p-mercuribenzoic acid for a thiol enzyme having a cysteine residue at an active site, and carbon monoxide and hydrogen cyanide for a heme enzyme such as catalase. A variety of inhibitor substances are found in animals and plants, and play an important role in the regulation mechanism or the metabolic pathway in a living body. For example, it is known that as the inhibitor for proteases such as trypsin, plasmin, chymotrypsin and cathepsin, there are present $\alpha$-1-antitrypsin, $\alpha$-2-macroglobulin ($\alpha$2M), chontrapsin, murinoglobulin, inter-$\alpha$-trypsin inhibitor, antithrombin-III (AT-III), heparin cofactor II, protein Ca inhibitor, $\alpha$-2-plasmin inhibitor, C1-inactivator, $\alpha$-1-antichymotrypsin and SH-proteinase inhibitor in animals. Furthermore, it is known that soybean trypsin inhibitor is present in plants. Moreover, inhibition of a dehydrogenase such as L-threonine dehydrogenase by L-isoleucine is an example of the metabolic regulation. As the inhibitor produced by microorganism, there can be mentioned leupeptin, antipain, chymostatin, elastatinal and phosphoramidon for proteases, panosialin for sialidase, pyridinedolol for $\beta$-galactosidase, oudenone for tyrosine hydroxylase, fusaric acid and dopastine for dopamine-$\beta$-hydroxylase, and isoflavone for DOPA decarboxylase. There are known many other inhibitor compounds chemically synthesized, though not specifically mentioned here, and thus the enzyme inhibitors are too numerous to mention.

The measured value of the enzyme activity in the presence of an enzyme inhibitor is equal to the value obtained by subtracting the portion of the enzyme activity deactivated by the enzyme inhibitor from the total enzyme activity. Accordingly, by using the enzyme inhibitor in a known amount, the total enzyme activity can be determined. In contrast, by using the enzyme in a known amount, the amount of the enzyme inhibitor can be determined. Furthermore, a known amount of the enzyme inhibitor or the enzyme can be added gradually, several times.

The above-mentioned enzyme or enzyme inhibitor can be used not only in the form of a refined single substance or a crude substance but also in the form of one component present in a living body sample.

By using one substrate-immobilized support column, according to the measurement method of the present invention, the activities of objective enzymes used in the same field can be compared, and a selection of enzymes can be made.

The kind of the substrate-immobilized support column to be used for the comparison of the enzyme activities is not critical, but all of the above-mentioned substrate-modified support columns can be used. For example, when arginine p-nitroanilide (Arg-pNA') ("p-nitroanilide" is hereinafter abbreviated as "p-NA'" when appropriate) or lysine p-nitroanilide (Lys-pNA') is used as the immobilized substrate, all enzymes having a specific action to arginine or lysine can be tested as the objective enzyme for the measurement, and the activities of the objective enzymes can be compared by detecting p-nitroaniline formed as the decomposition products in amounts corresponding to the activities of the respective enzymes. As the objective enzyme, the activity of which is to be composed by the Arg-pNA' immobilized support column, there can be mentioned thrombin, trypsin, XIa factor, XIIa factor, Xa factor, kallikrein and urokinase. When the Lys-pNA'-immobilized support column is used, the activities of plasmin, kallikrein and enterokinase can be compared. This comparison method can be applied not only to known proteases having a specific action to arginine or lysin, as mentioned above, but also to a variety of unknown proteases and other enzymes.

Many enzymes greatly differing in activity, although having substantially the same substrate specificity, are known. The enzyme selection method of the present invention can be used as a simple method of discriminating and identifying enzyme. More specifically, the method of the present invention can be used as a simple screening method of selecting an enzyme having a peculiar substrate specificity from among many enzymes or as a simple screening method of determining the intensity of the activity to this peculiar substrate. Moreover, the method of the present invention can be used for determining the activity of a certain enzyme at respective steps of the purification process. Furthermore, by using a plurality of substrate-immobilized support columns, the difference of the specificity can be examined with respect to specific enzymes, or in contrast, a novel enzyme can be identified based on the difference of the specificity. Accordingly, the objective enzyme, the activity of which is to be measured, can be in the form of a purified single product or a crude product, or may be one component present in a living body sample. As the same use of enzymes to which the selection method of the present invention is applied, there can be mentioned the use of industrial enzymes for foodstuffs and detergents, the use of enzymes for medicines or for clinical analysis, and the use of enzymes for genetic engineering.

The present invention will now be described in detail with reference to the following examples, given only for illustration and in no way limiting the scope of the invention.

EXAMPLE 1

A hydroxyl group-modified bead obtained from glycidyl methacrylate and ethylene glycol dimethacrylate was reacted with 1,4-butanediol diglycidyl ether in 1M NaOH aqueous solution to introduce an epoxy group to the hydroxyl group-modified bead, and then a carboxyl group introduced thereto by using γ-aminobutyric acid. The obtained bead was thoroughly washed with anhydrous dioxane to obtain a carboxyl-modified bead, and N-hydroxysuccinimide and dicyclohexylcarbodiimide were added to the carboxyl-modified bead in anhydrous dioxane. The reaction was carried out under shaking at room temperature for 1.5 hours, the formed bead was recovered by filtration and was rapidly washed with anhydrous dioxane and methanol, 1 g of the obtained bead was added to 3 ml of 0.01N carbonate buffer (pH 9.4) containing 30 mg of arginine p-nitroanilide (Arg-pNA'), the reaction was carried out under shaking at room temperature for 2 hours, and the reaction mixture was allowed to stand at 4° C. overnight. The bead was recovered by filtration and washed with a 1M aqueous solution of sodium chloride and water, and it was confirmed that the obtained Arg-pNA' immobilized bead contained about 10 μmoles per g of the dry bead having Arg-pNA' supported thereon.

Figure 2:
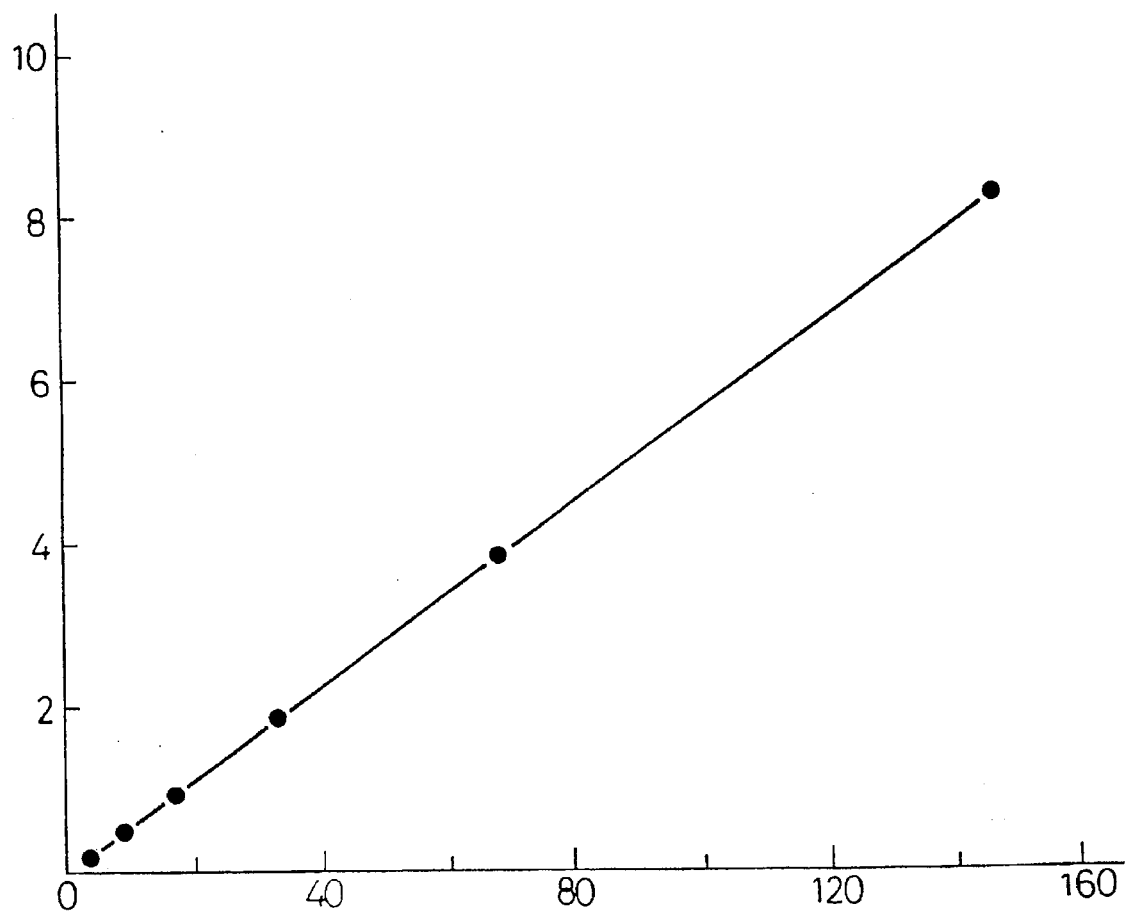
FIG. 2 illustrates the relationship between the activity value of injected trypsin and the measured value, in which the peak area ($\times 10^{-3}$=p-nitroaniline µmole) of p-nitroaniline (hereinafter abbreviated as "p-NA" when appropriate), the decomposition product, is plotted on the ordinate and the activity (BAEE nkat/3 µl) of injected trypsin is plotted on the abscissa.

The obtained Arg-pNA'-immobilized bead was packed in a stainless steel column having an inner diameter of 4.6 mm and a length of 1.0 cm to obtain an Arg-pNA'-immobilized column. Separately, the carboxyl-modified bead was packed in a stainless steel column having an inner diameter of 4.6 mm and a length of 3.5 mm to obtain a separation column. The Arg-pNA'-immobilized column and the separation column were assembled in a high-speed liquid chromatography apparatus, as shown in FIG. 1, in which the separation column was additionally disposed between a column 4 and a detector 5, and the activity of trypsin was measured and the detection limit of the measurement in the present apparatus, the linearity and the flow rate dependency were determined.
(1) Limit of detection of activity of trypsin in present apparatus and linearity of measured values With an increase of the activity value of trypsin injected into the present apparatus, the detected measured value rose linearly and a good correlation was found, as shown in FIG. 2, wherein the abscissa indicates the activity (BAEE nkat/3 μl) of the injected trypsin and the ordinate indicate the peak area ($\times 10^{-3}$=pNA μmole) of pNA. The detection limit was 0.05 nkat. The chromatography conditions adopted were as described below.

Eluent: 50 mM tris-hydrochloric acid buffer solution (pH 7.4)+0.15M NaCl (eluent A)

Flow rate: 1 ml/min

Detection: 405 nm

Sample: Trypsin (supplied by Sigma), BAEE (benzoylarginine ethyl ester) nkat/3 μl of eluent A+0.5 mM $CaCl_2$ (the activity of trypsin was expressed by the hydrolysis activity to BAEE, and 1 BAEE nkat was the quantity of the enzyme activity for decomposing 1 nmole of BAEE for 1 second)

Measurement temperature: 25° C.

(2) Flow rate dependency of measured values

A predetermined amount of trypsin was injected into the present apparatus, and the dependency of the measured values on the flow rate was examined. The results are shown in FIG. 3 wherein the abscissa indicates the flow rate (ml/min) and the ordinate indicates the peak area ($\times 10^{-4}$= pNA μmole) of pNA.

The chromatography conditions were the same as described in (1) above except that the flow rate was changed.

Figure 3:
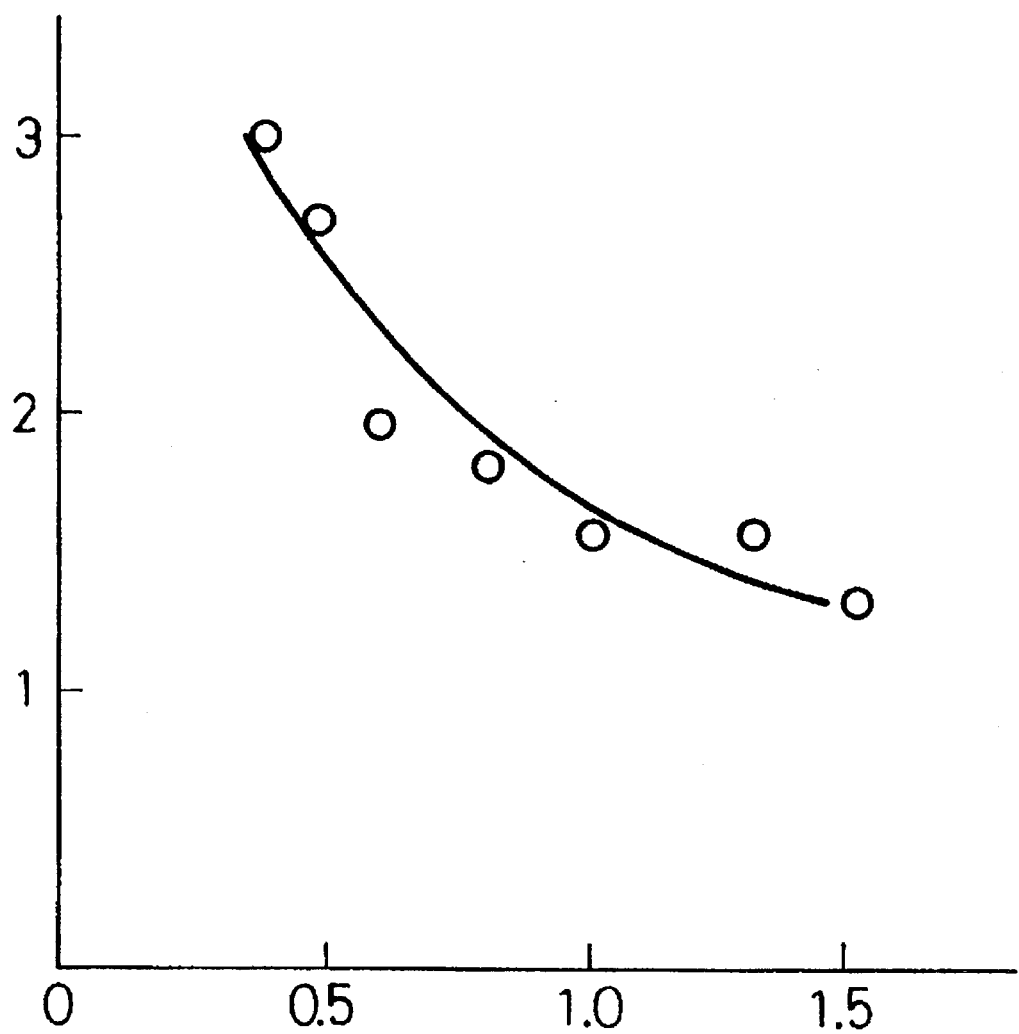
FIG. 3 illustrates the relationship between the flow rate and the measured value, in which the peak area ($\times 10^{-4}$=pNA µmole) of pNA is plotted on the ordinate and the flow rate (ml/min) is plotted on the abscissa.

As shown in FIG. 3, a tendency for the value to decrease in inverse proportion to an increase of the flow rate was observed.

(3) Temperature dependency of measured values

Figure 4:
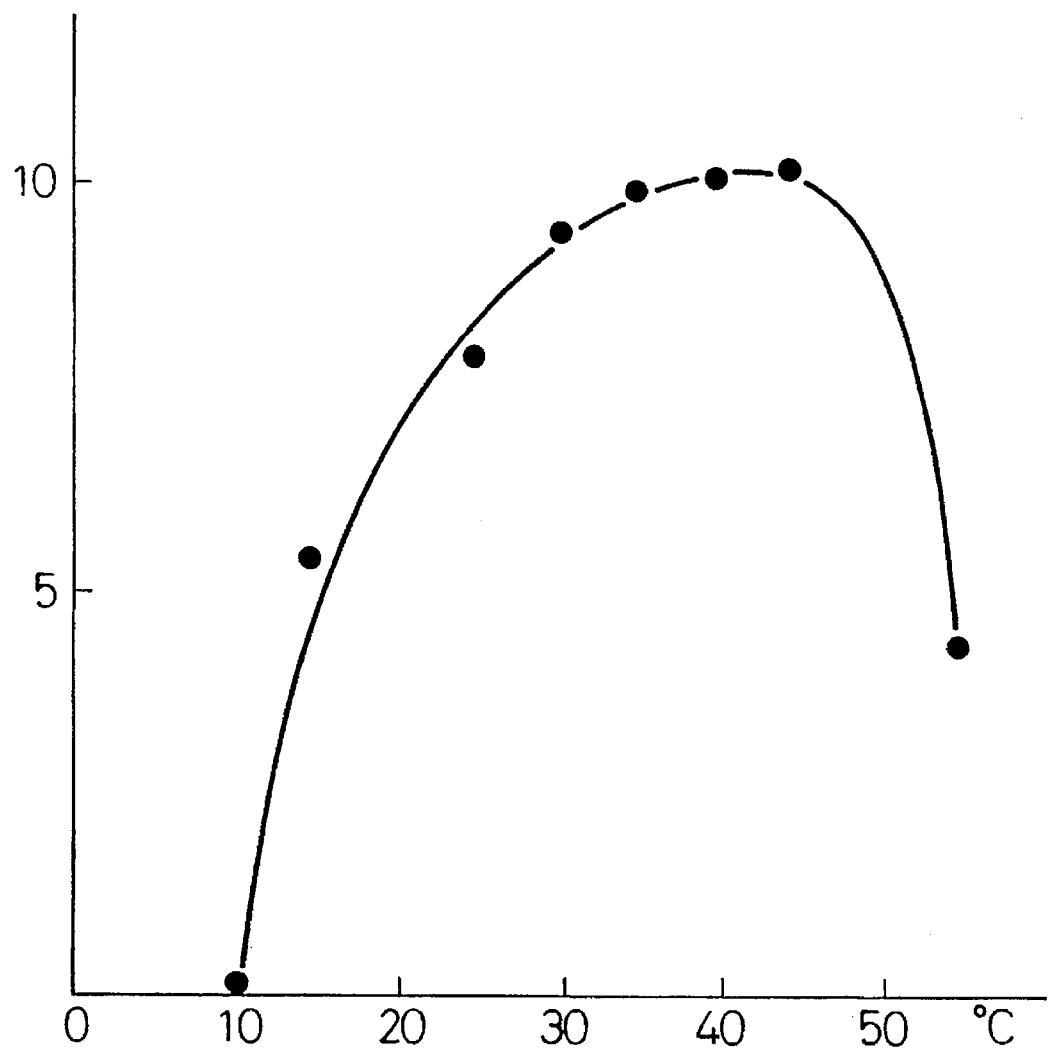
FIG. 4 illustrates the relationship between the temperature and the measured value, in which the peak area ($\times 10^{-4}$=pNA µmole) is plotted on the ordinate and the temperature (°C.) is plotted on the abscissa.

A predetermined amount of trypsin was injected into the present apparatus, and the dependency of the measured values on the temperature was examined. The results are shown in FIG. 4, wherein the abscissa indicates the temperature (°C.) and the ordinate indicates the peak area ($\times 10^{-4}$=pNA μmole). The chromatography conditions were the same as described in (1) above, except that the temperature was varied. As shown in FIG. 4, it was found that the measured value was largest at a column temperature of about 40° C.

(4) Salt Concentration Dependency of Measured Values

Figure 5:
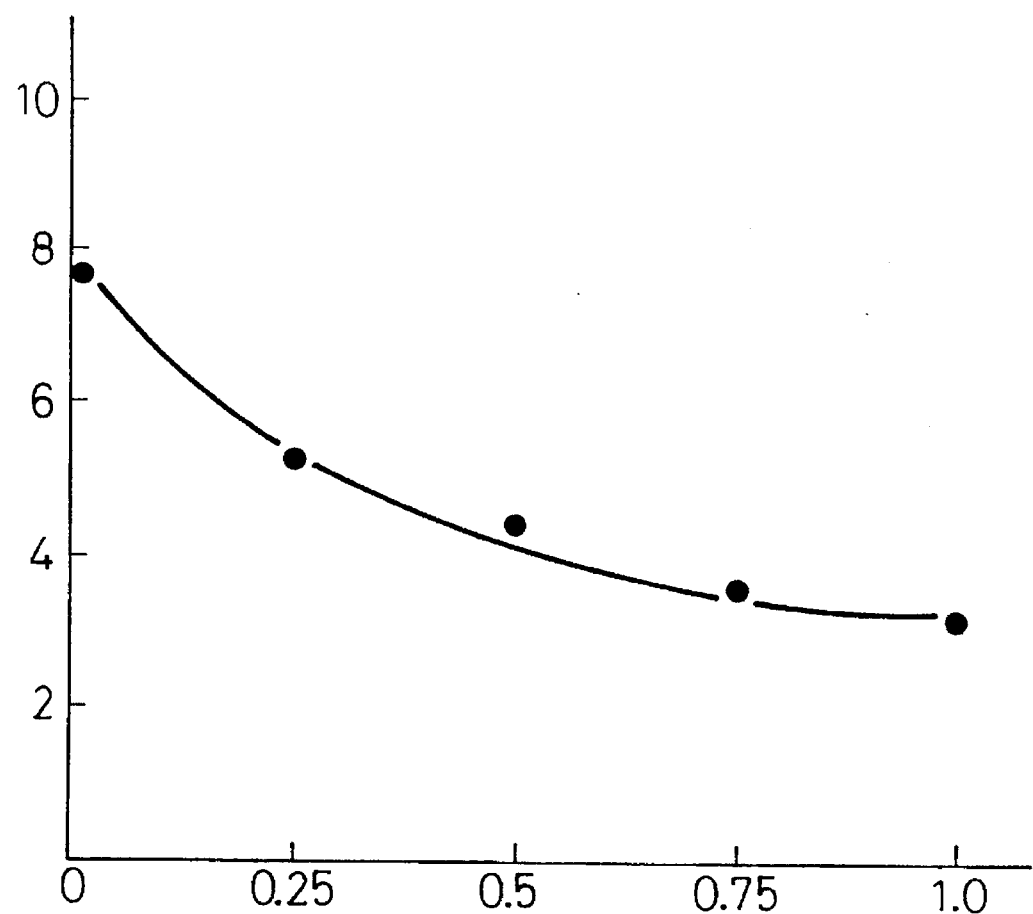
FIG. 5 illustrates the relationship between the concentration of sodium chloride contained in an eluent and the measured value, in which the peak area ($\times 10^{-4}$=pNA µmole) is plotted on the ordinate and the molar concentration (M) is plotted on the abscissa.

A predetermined amount of trypsin was injected into the present apparatus and the dependency of the measured values on the salt concentration was examined. The results are shown in FIG. 5, wherein the abscissa indicates the molar concentration (M) and the ordinate indicates the peak area ($10^{-4}$=pNA μmole). The chromatography conditions were the same as those described in (1) above.

As shown in FIG. 5, a tendency for the measured value to decrease with an increase of the salt concentration was observed.

EXAMPLE 2

Figure 6:
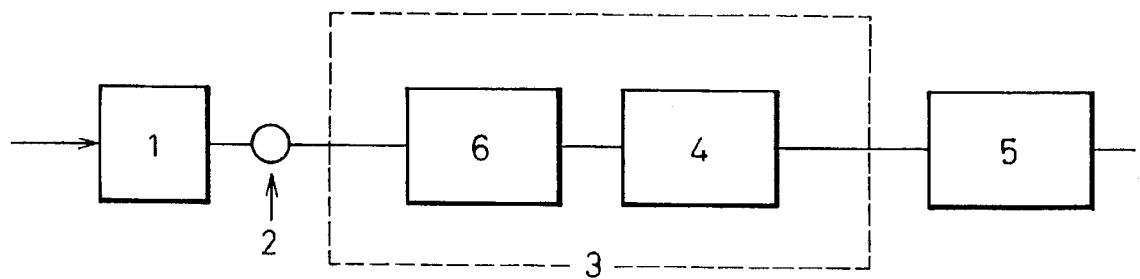
FIG. 6 illustrates another example of the apparatus for measuring the enzyme activity according to the present invention, in which a separation column is connected to a substrate column, wherein 1 represents a pump, 2 represents a sample, 3 represents a thermostat oven, 4 represents a column of a support having a substrate immobilized thereon, 5 represents a detector, and 6 represents a separation column.
Figure 7:
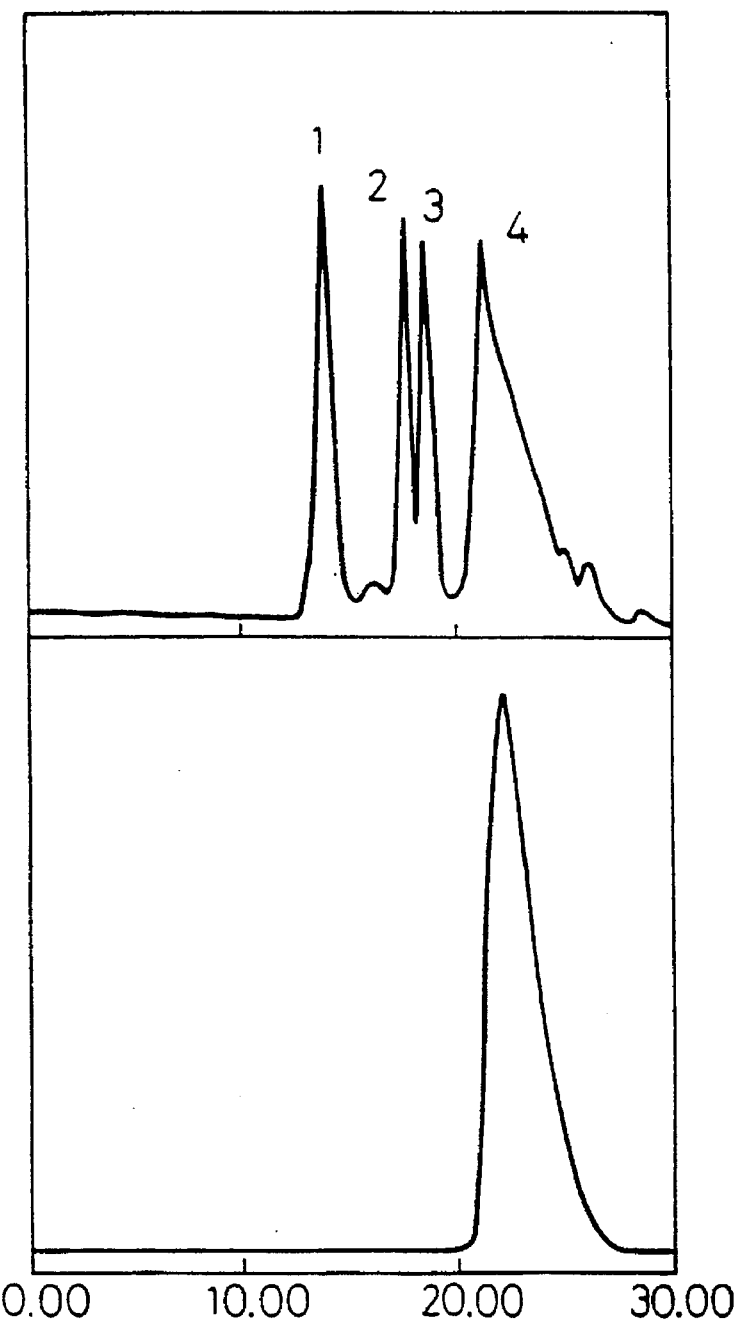
FIG. 7 shows chromatograms obtained when a separation column is connected to a substrate column, in which FIG. 7-(1) shows a protein separation pattern (by the absorption at 280 nm) and FIG. 7-(2) shows the activity of trypsin (the peak of pNA by the absorption at 405 nm), ①, ②, ③ and ④ represent peaks of thyroglobulin, transferrin, ovalbumin and trypsin, respectively, and the elution time (minutes) is plotted on the abscissa and the absorbance is plotted on the ordinate.

The Arg-pNA'-immobilized bead obtained in Example 1 was packed in a stainless steel column having an inner diameter of 4.6 mm and a length of 1.0 cm to obtain an Arg-pNA'-immobilized column. Separately, two commercially available gel filtration separation columns (WS-803 supplied by Showa Denko) having an inner diameter of 8.0 mm and a length of 30 cm were connected to each other to obtain a separation column. As shown in FIG. 6, the separation column 6 and the Arg-pNA'-immobilized column 4 were assembled in a high-speed liquid chromatography, and an ultraviolet absorption detector and a visible absorption detector were disposed as the detector 5. A mixture 2 of four proteins (thyroglobulin, transferrin, ovalbumin and trypsin)

was injected into the present apparatus, and the separation pattern of the proteins was detected by the absorption at 280 nm and the trypsin activity was detected by the absorption at 405 nm. The results are shown in FIG. 7, wherein FIG. 7-(1) shows a protein separation pattern by the absorption at 280 nm and FIG. 7-2 shows the activity of trypsin, i.e., the peak of pNA by the absorption at 405 nm. In FIG. 7-(1), ①, ②, ③ and ④ represent peaks of thyroglobulin, transferrin, ovalbumin and trypsin, respectively. As seen from FIG. 7, the separation of several proteins (FIG. 7-(1)) and the detection of the trypsin activity (FIG. 7-(2)) was simultaneously performed by the present apparatus.

The chromatography conditions adopted were as described below.

Eluent: 50 mM tris-hydrochloric acid buffer solution (pH 7.4)+0.15M NaCl

Flow rate: 1 ml/min

Detection: (1) 280 nm, (2) 405 nm

Sample: thyroglobulin (bovine, type I, supplied by Sigma), transferrin (human, supplied by Sigma), ovalbumin (supplied by Sigma), trypsin (bovine spleen, type III, supplied by Sigma)

Measurement temperature: 25° C.

EXAMPLE 3

Figure 8:
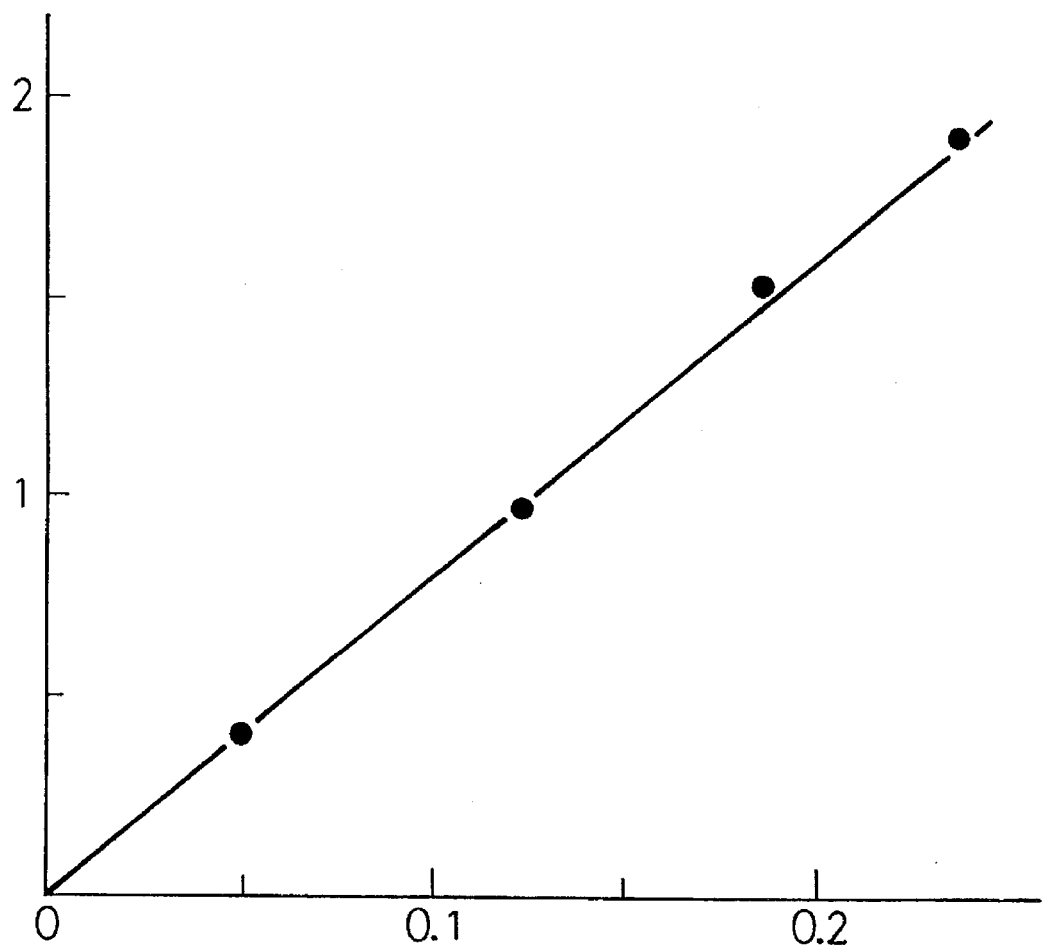
FIG. 8 illustrates the relationship between the activity value of injected thrombin and the obtained measured value, in which the peak area of pNA is plotted on the ordinate and the activity (NIH unit) of injected thrombin is plotted on the abscissa.

The linearity of the measured values of thrombin in the present apparatus was examined in the same manner as described in Example 1 except that D-phenyl-pipecolylarginine p-nitroanilide was used instead of arginine p-nitroanilide and thrombin was used instead of trypsin. It was found that the detected measured value rose linearly with an increase of the activity value of thrombin injected in the present apparatus and a good correlation was established, as shown in FIG. 8, wherein the abscissa indicates the activity (NIH unit) of injected thrombin and the ordinate indicates the peak area of pNA. Note, the chromatography conditions adopted were as described below.

Eluent: 50 mM tris-hydrochloric acid buffer solution (pH 7.4)+0.15M NaCl

Flow rate: 1 ml/min

Detection: 405 nm

Sample: thrombin (human plasma, supplied by Sigma), 260 NIH units/5 µl of 50 mM sodium citrate (pH 6.5)+0.15M NaCl Measurement temperature: 25° C.

EXAMPLE 4

The S-2238-immobilized bead prepared in Example 3 was packed in a stainless steel column having an inner diameter of 4.6 mm and a length of 1.0 cm to obtain an S-2238-immobilized column. Separately, the carboxyl-modified bead was packed in a stainless steel column having an inner diameter of 4.6 mm and a length of 3.5 cm to obtain a separation column. The S-2238-immobilized column and the separation column were assembled in a high-speed liquid chromatography apparatus.

Figure 9:
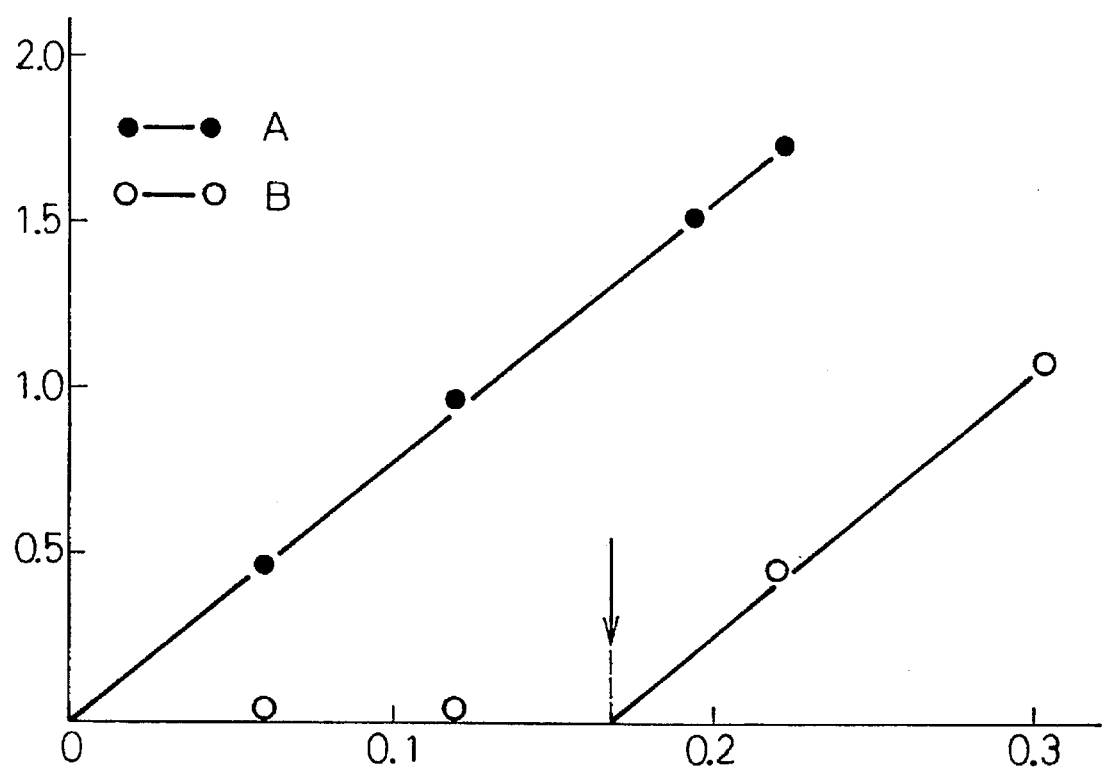
FIG. 9 shows the binding ratio between thrombin and AT-III, determined by an enzyme activity-measuring apparatus of the present invention, in which the activity (NIH unit) of thrombin injected in the measuring apparatus is plotted on the abscissa and the detected pNA area is plotted on the ordinate, and A indicates the measurement in the absence of AT-III and B indicates the measurement in the presence of AT-III.

A buffer solution (50 mM tris-hydrochloric acid buffer solution having a pH value of 7.4 and containing 0.15M NaCl), in which 1.3, 2.6, 5.2 or 6.6 NIH units of thrombin was incorporated, was prepared, and 80 µl of this solution was added to 30 µl of the same buffer solution containing a predetermined amount (about 1.5 NIH units) of AT-III. The sample was allowed to stand at 25° C. for 3 minutes, 5 µl of the sample was injected into the present apparatus, and the peak of released p-nitroaniline (pNA) was detected. Separately, thrombin was added to 30 µl of the above-mentioned buffer solution containing no AT-III, and the above operations were similarly conducted to obtain a blank. The thrombin activity value of each sample was detected by the present apparatus, and the results are shown in FIG. 9, wherein the abscissa indicates the activity (NIH unit) of thrombin and the ordinate indicates the detected pNA peak area. As seen from FIG. 9, by comparing the thrombin activity values B and A, obtained in the presence and absence of AT-III, respectively, it was confirmed that AT-III present in 5 µl of the sample inhibited 0.17 NIH unit of thrombin.

Note, the chromatography conditions adopted were as described below.

Eluent: 50 mM tris-hydrochloric acid buffer solution (pH 7.4), +0.15M NaCl

Flow rate: 1 ml/min

Detection: 405 nm

Sample: At-III (human plasma, supplied by Sigma), Thrombin (human plasma, supplied by Sigma)

Measurement temperature: 25° C.

EXAMPLE 5

The Arg-pNA'-immobilized column and the separation column, prepared in Example 1, were assembled in a high-speed liquid chromatography apparatus.

A buffer solution (50 mM tris-hydrochloric acid buffer solution having a pH value of 8.4) containing 0, 3, 9, 12, 14 or $16 \times 10^{-2}$ nmole of trypsin was prepared, and 0.2 ml of this buffer solution was added to 0.8 ml of the same buffer solution containing a predetermined amount ($12 \times 10^{-2}$ nmole) of α2M. The sample was allowed to stand at room temperature for 1 minute, 0.5 ml of the sample was injected into the present apparatus, and the peak of the released pNA was detected. Separately, trypsin was added to 0.8 ml of the above-mentioned buffer solution containing no α2M, and the above operations were similarly conducted to obtain a blank.

Figure 10:
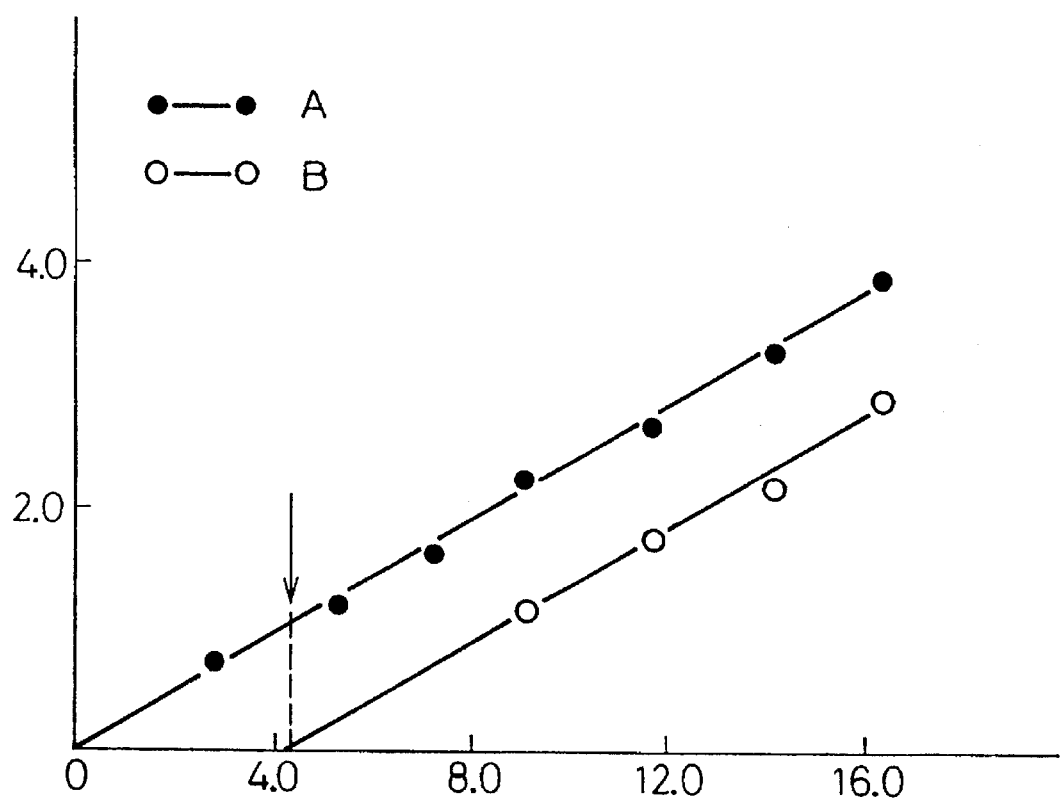
FIG. 10 illustrates the binding ratio between α2M and trypsin, determined by using an enzyme activity-measuring apparatus of the present invention, in which the concentration ($\times 10^{-2}$ nmole) of trypsin injected into the measuring apparatus is plotted on the abscissa and the detected pNA peak area is plotted on the ordinate, and A indicates the measurement in the absence of α2M and B indicates the measurement in the presence of α2M.

The trypsin activity value of each sample detected by the present apparatus is shown in FIG. 10, wherein the abscissa indicates the concentration ($\times 10^{-2}$ nmole) of trypsin and the ordinate indicates the detected pNA peak area. It was found that, by comparing the trypsin activity values B and A, obtained in the presence and absence of α2M, respectively, trypsin was bonded to α2M present in the sample at an α2M/trypsin ratio of 3/1.

The chromatography conditions adopted were as described below.

Eluent: 50 mM tris-hydrochloric acid buffer solution (pH 8.4)

Flow rate: 1 ml/min

Detection: 405 nm

Sample: Trypsin (bovine spleen, supplied by Sigma), α2M (human, supplied by Sigma)

Measurement: 25° C.

EXAMPLE 6

The Arg-pNA'-immobilized column and the separation column, prepared in Example 1, were assembled in a high-speed liquid chromatography apparatus.

Figure 11:
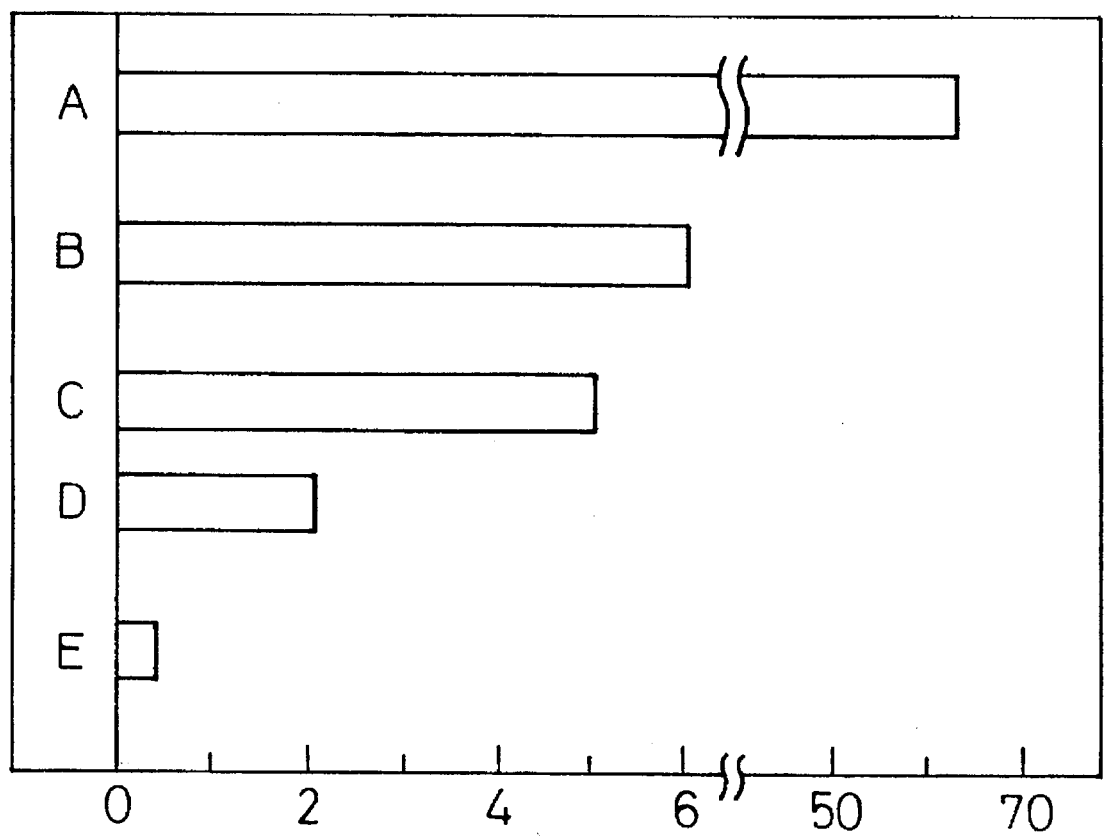
FIG. 11 shows the enzyme activity values detected by an enzyme activity-measuring apparatus of the present invention, in which the detected pNA peak area is plotted on the abscissa and A, B, C, D and E represent the results obtained with respect to trypsin, urokinase, human thrombin, bovine thrombin and kallikrein, respectively.
Figure 12A:
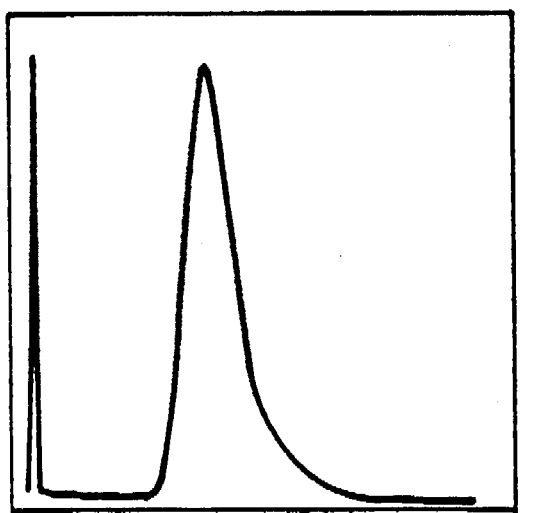
FIG. 12 shows the thrombin activity values detected by an enzyme activity-measuring apparatus of the present invention, in which the elution time (minutes) is plotted on the abscissa and the absorption of pNA at 405 nm is plotted on the ordinate, and A, B, C and D represent the results obtained with respect to thrombins derived from human, mouse, rat and bovine, respectively.
Figure 12B:
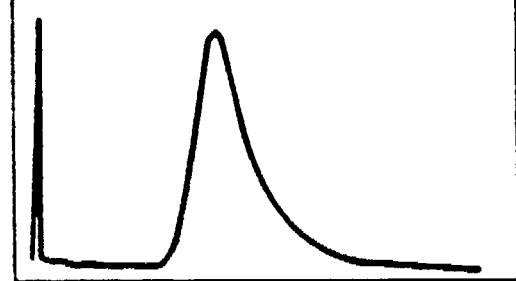
Figure 12C:
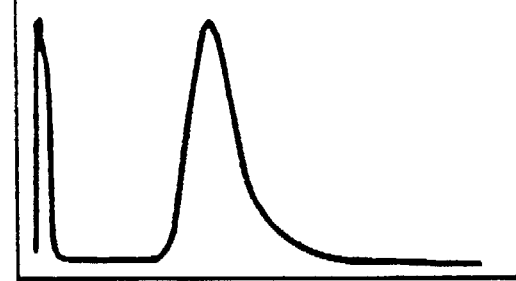
Figure 12D:
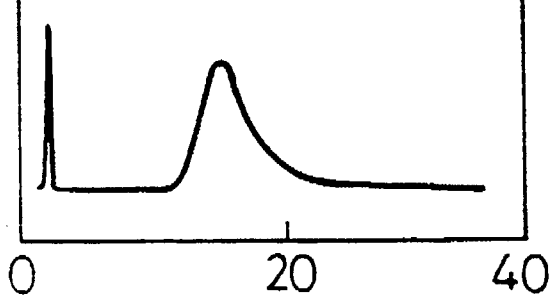

First, 1 ml of a buffer solution (50 mM tris-hydrochloric acid buffer solution having a pH value of 7.4) containing 1 mg of trypsin, urokinase, thrombin (derived from human and bovine) or kallikren was prepared, 5 μl of the solution was injected into the present apparatus, and the peak of the released p-nitroaniline (pNA) was detected and compared. The results are shown in FIG. 11, wherein the abscissa indicates the detected pNA peak area and A, B, C, D and E represent the results obtained with respect to trypsin, urokinase, human thrombin, bovine thrombin and kallikren, respectively. It was found that trypsin had a highest pNA-separating activity to the Arg-pNA'-immobilizing column and the activity was higher in the order of urokinase, human thrombin, bovine thrombin, and kallikrein.

The chromatography conditions adopted were as described below.

Eluent: 50 mM tris-hydrochloric acid buffer solution (pH 7.4)+0.15M NaCl

Flow rate: 1 ml/min

Detection: 405 nm

Sample: Trypsin (bovine, supplied Sigma), urokinase (human supplied by Sigma), thrombin (human and bovine, supplied by Sigma), kallikren (kallidinogenase reference product supplied by National Institute of Hygienic Science, Japan)

Measurement temperature: 25° C.

EXAMPLE 7

The S-2238-immobilized column and the separation column, prepared in Example 1, were assembled in a high-speed liquid chromatography apparatus.

First, 1 ml of a buffer solution (50 mA tris-hydrochloric acid buffer solution having a pH value of 7.4) containing 1 mg of thrombin derived from human, mouse, rat or bovine was prepared, 5 μl of the solution was injected to the present apparatus, and the released pNA was detected. The results are shown in FIG. 12, wherein the abscissa indicates the elution time (min) and the ordinate indicates the absorption of pNA at 405 nm, and A, B, C and D represent the results obtained with respect to thrombins derived from human, mouse, rat and bovine, respectively. It was found that the human/mouse/rat/bovine pNA peak area ratio was 4/2/2/1.

The chromatography conditions adopted were as described below.

Eluent: 50 mM tris-hydrochloric acid buffer solution (pH 7.4)+0.15M NaCl

Flow rate: 1 ml/min

Detection: 405 nm

Sample: Thrombin (human, mouse, rat and bovine, supplied by Sigma)

Measurement temperature: 25° C.

EXAMPLE 8

Figure 13:
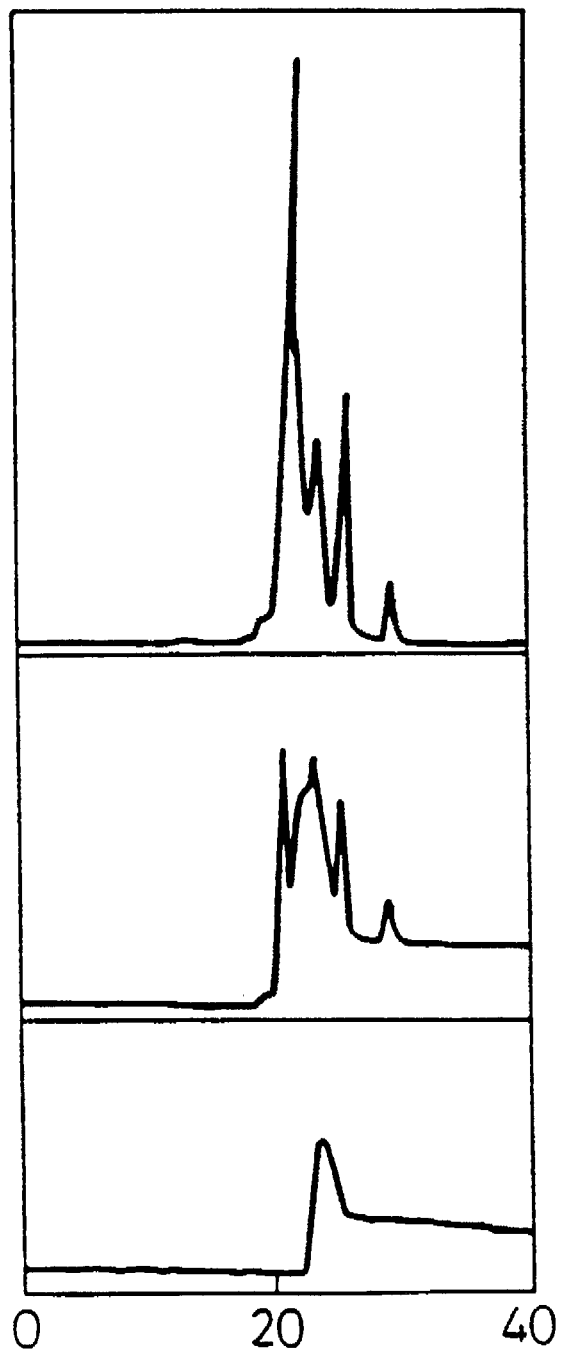
FIG. 13 shows the results of a separation and activity detection of enzyme in pancreatin, made by an enzyme activity-measuring apparatus of the present invention, in which FIG. 13-(1) shows the results obtained when pancreatin is injected in a separation column and the detection is made at 230 nm and FIGS. 13-(2) and 13-(3) show the results obtained when pancreatin is injected into the measurement system of the present invention comprising a substrate-immobilized column connected to a separation column and the detection is made at 230 nm and 405 nm, respectively, and the retention time (minutes) is plotted on the abscissa and the absorbance is plotted on the ordinate.

Two commercially available gel filtration columns, WS-803F (inner diameter=8 mm, length=30 cm, supplied by Showa Denko), were connected to each other to form a separation column. The Arg-pNA'-immobilized column (inner diameter=4.6 mm, length=1.0 cm) prepared in Example 1 was connected to the rear part of the separation column. The separation column and the Arg-pNA'-immobilized column were assembled in a high-speed liquid chromatography apparatus, and pancreatin was injected into the apparatus. The separation pattern of substances in pancreatin was detected based on the absorption at 230 nm, and the Arg-pNA' decomposition activity was detected based on the absorption at 405 nm. The results are shown in FIG. 13, wherein the abscissa indicates the retention time (min) and the ordinate indicates the FIG. 13-(1) shows the results obtained when pancreatin is injected in a separation column and the detection is made at 230 nm and FIGS. 13-(2) and 13-(3) show the results obtained when pancreatin is injected into the measurement system of the present invention comprising a substrate-immobilized column connected to a separation column and the detection is made at 230 nm and 405 nm, respectively. From FIG. 13, it is seen that the separation of several substances present in pancreatin [FIG. 13-(2)] and the detection of the Arg-pNA' decomposition activity [FIG. 13-(3)] were simultaneously accomplished by the present apparatus. When the separation pattern obtained by using the substrate-immobilized column as the post column connected to the separation column [FIG. 13-(2)] was compared with the separation pattern obtained by using only the separation column [FIG. 13-(1)], it is seen that the peak where the enzyme activity was present was tailing. Accordingly, it was confirmed that a specific enzyme activity was detected by the change of the retention time in the column.

The chromatography conditions adopted were as described below.

Eluent: 50 mM tris-hydrochloric acid buffer solution (pH 7.4)+0.15M NaCl

Flow rate: 1 ml/min

Detection: 230 nm and 405 nm

Sample: pancreatin (supplied by ICN)

Measurement temperature: 25° C.

What is claimed is:

1. A method for measuring enzyme activity, which consists essentially of introducing an enzyme, the activity of which is to be measured, into a high pressure liquid chromatography (HPLC) column comprising a hollow tube packed with a filler comprising (A) a support composed of hard beads and (B) a substrate that can be recognized by the enzyme and that is immobilized by a covalent bond on the support, wherein the substrate is a substrate that is capable of forming a substrate decomposition product by contacting with the enzyme while the enzyme is passing through the column, and the substrate decomposition product is solubilized by the activity of the enzyme so that the substrate decomposition product can pass through a detector, and measuring the amount of the obtained decomposition product of the substrate by detecting the decomposition product wherein no further enzymatic reactions occur beyond the above said contacting with the enzyme which formed the above said substrate decomposition product.

2. A method for selecting enzymes, which consists essentially of introducing enzymes, the activities of which are to be measured and which all recognize a particular substrate from which a particular substrate decomposition product can be formed after the substrate is contacted with any of the enzymes, into a high pressure liquid chromatography (HPLC) column comprising a hollow tube packed with a filler comprising (A) a support composed of hard beads and (B) a substrate that can be recognized by the enzymes and that is immobilized by a covalent bond on the support, wherein the substrate is a substrate that is capable of forming a substrate decomposition product by contacting with the enzyme, and the substrate decomposition product is solubilized by the activity of the enzyme so that the substrate decomposition product can pass through a detector, and measuring the amounts of the obtained decomposition product of the substrate by detecting the decomposition product wherein no further enzymatic reactions occur beyond the above said contacting with the enzyme which formed the above said substrate decomposition product to compare the activities of the enzymes with one another.

3. A method for measuring enzyme activity according to claim 1, wherein the introduction of the enzyme into the column is effected in the presence of an inhibitor capable of inhibiting the activity of said enzyme, and the amount of the obtained decomposition product of the substrate is measured to determine the residual activity of the enzyme.

4. A method for measuring enzyme activity according to claim 1, wherein the substrate is bonded to the support through a binding group having a length corresponding to 6 to 30 atoms.

5. A method for measuring enzyme activity according to claim 1, wherein the substrate is selected from the group consisting of an amine, a saccharide, a labelled saccharide, cholesterol, choline, chondroitin sulfate, (deoxy)-ribonucleic acid, a phosphoric acid monoester, an amino acid, an oligopeptide, a labelled amino acid, and a labelled oligopeptide.

\* \* \* \* \*